US010007993B2

United States Patent
Takahashi (10) Patent No.: US 10,007,993 B2
(45) Date of Patent: Jun. 26, 2018

(54) INSPECTION DEVICE, INSPECTION METHOD, AND COMPUTER READABLE MEDIUM STORING PROGRAM CAUSING COMPUTER TO PERFORM INSPECTION METHOD

(71) Applicant: FUJIFILM Corporation, Minato-Ku, Tokyo (JP)

(72) Inventor: Ippei Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/247,512

(22) Filed: Aug. 25, 2016

(65) Prior Publication Data
US 2016/0364868 A1 Dec. 15, 2016

Related U.S. Application Data

(63) Continuation of application No. PCT/JP2015/051503, filed on Jan. 21, 2015.

(30) Foreign Application Priority Data

Feb. 28, 2014 (JP) .................. 2014-038727

(51) Int. Cl.
*G06K 9/00* (2006.01)
*G06T 7/00* (2017.01)
(Continued)

(52) U.S. Cl.
CPC ........... *G06T 7/0042* (2013.01); *G01M 7/025* (2013.01); *G01N 21/9508* (2013.01);
(Continued)

(58) Field of Classification Search
CPC ............ G06K 9/00; G06T 7/00; G01N 21/00
(Continued)

(56) References Cited

U.S. PATENT DOCUMENTS 6,883,681 B1   4/2005 Coughlin et al.
7,519,148 B2 * 4/2009 Kotowski .............. G01N 23/04
                                                        378/198

(Continued)

FOREIGN PATENT DOCUMENTS

JP          6255755 A     9/1994
JP       2001335145 A    12/2001
(Continued)

OTHER PUBLICATIONS

Communication dated Jan. 23, 2017, from the European Patent Office in counterpart European Application No. 15755144.1.
(Continued)

*Primary Examiner* — Abolfazl Tabatabai
(74) *Attorney, Agent, or Firm* — Sughrue Mion, PLLC (57) ABSTRACT

An inspection device 1 includes an inspection table 2 on which an inspection target T which is a set of a plurality of solid drugs O is placed, a vibration unit 3 that vibrates the inspection table 2, an imaging unit 4 that acquires an image of the inspection target T, which is placed on the inspection table 2, in a first direction along the inspection table 2, and a control unit 5 that determines whether the solid drugs O in the inspection target T overlap each other, based on inspection target information including appearance information of each of the drugs forming the inspection target T and the image of the inspection target T in the first direction, and operates the vibration unit 3 in a case in which it is determined that the solid drugs O overlap each other.

15 Claims, 6 Drawing Sheets

(51) Int. Cl.
 *G01N 21/95* (2006.01)
 *G01M 7/02* (2006.01)
 *G06T 7/73* (2017.01)
 *H04N 7/18* (2006.01)

(52) U.S. Cl.
 CPC ............ *G06T 7/001* (2013.01); *G06T 7/0004* (2013.01); *G06T 7/0008* (2013.01); *G06T 7/73* (2017.01); *G06T 2207/30242* (2013.01)

(58) Field of Classification Search
 USPC ............ 382/103, 236; 348/86, 169, 352, 92; 53/52, 64
 See application file for complete search history.

(56) References Cited

U.S. PATENT DOCUMENTS

| | | |
|---|---|---|
| 2012/0200596 A1 | 8/2012 | Gotou et al. |
| 2012/0216485 A1* | 8/2012 | Amano ................... G07F 11/44 53/64 |
| 2013/0342676 A1 | 12/2013 | Amano et al. |
| 2014/0002631 A1 | 1/2014 | Amano et al. |
| 2014/0033644 A1 | 2/2014 | Amano et al. |

FOREIGN PATENT DOCUMENTS

| | | |
|---|---|---|
| JP | 2003-526395 A | 9/2003 |
| JP | 201086257 A | 4/2010 |
| JP | 2011-104077 A | 6/2011 |
| JP | 2013-39289 A | 2/2013 |
| JP | 2013-66533 A | 4/2013 |
| JP | 2013-78420 A | 5/2013 |
| JP | 2013-144101 A | 7/2013 |
| WO | 2004112685 A1 | 12/2004 |
| WO | 2012005004 A1 | 1/2012 |

OTHER PUBLICATIONS

International Search Report dated Feb. 24, 2015 issued by the International Searching Authority in counterpart International Application No. PCT/JP2015/051503 (PCT/ISA/210).
Written Opinion dated Feb. 24, 2015 issued by the International Searching Authority in counterpart International Application No. PCT/JP2015/051503 (PCT/ISA/237).
Office Action dated Dec. 20, 2016, by the Japanese Patent Office in counterpart Japanese Application No. 2014-038727.

* cited by examiner

INSPECTION DEVICE, INSPECTION METHOD, AND COMPUTER READABLE MEDIUM STORING PROGRAM CAUSING COMPUTER TO PERFORM INSPECTION METHOD

CROSS REFERENCE TO RELATED APPLICATION

This is a continuation of International Application No. PCT/JP2015/051503 filed on Jan. 21, 2015, and claims priority from Japanese Patent Application No. 2014-038727 filed on Feb. 28, 2014, the entire disclosures of which are incorporated herein by reference.

BACKGROUND OF THE INVENTION

1. Field of the Invention

The present invention relates to an inspection device, an inspection method, and a computer readable medium storing a program that causes a computer to perform the inspection method.

2. Description of the Related Art

In some cases, each set of a plurality of articles is packaged into a packet and it is checked whether articles have been exactly inserted into each packet.

For example, a dispensing operation which is performed in hospital facilities or pharmacies packages a plurality of drugs corresponding to a dose into one packet. In the packaging process, it is necessary to package the exact number of drugs into each packet according to a prescription. For example, for solid drugs, such as capsules or tablets, the number of drugs to be packaged into each packet is checked.

JP2011-104077A discloses a drug dispensing device that captures an image of a plurality of drugs which correspond to one packet and are placed on an inspection table in a direction in which the inspection table is seen straight, while vibrating the inspection table having the plurality of drugs placed thereon and performs an outline extraction process for the obtained image to count the number of drugs. Then, the drug dispensing device compares the counted number of drugs with a prescription and displays a warning message on a screen of a monitor in a case in which the count value of the drugs is different from the prescription.

SUMMARY OF THE INVENTION

In a case in which drugs overlap each other, the drug dispensing device disclosed in JP2011-104077A detects a narrow portion which is generated in the outline of a drug group in the captured image and calculates the number of drugs forming a group on the basis of the number of narrow parts. However, in some cases, a distinct narrow portion is not generated in the outline of the drug group according to the state of the overlap between the drugs. In this case, a counting error is likely to occur.

In order to improve the accuracy of counting the number of drugs, the drug dispensing device disclosed in JP2011-104077A captures an image of drugs a plurality of times, counts the number of drugs from each of a plurality of obtained images, and determines a maximum value among the numbers of drugs as the count value of the drugs. As the number of imaging operations increases, the vibration time required for the inspection table increases. As a result, the probability of the overlap between drugs being removed increases and the accuracy of counting the number of drugs increases. However, since the time required to inspect each packet increases, inspection efficiency is reduced.

The invention has been made in view of the above-mentioned problems and an object of the invention is to provide an inspection device and an inspection method which can suitably and effectively arrange a plurality of articles on an inspection table and a program which causes a computer to perform the inspection method.

(1) An inspection device comprises an inspection table on which an inspection target which is a set of a plurality of articles is placed, a vibration unit that vibrates the inspection table, an imaging unit that acquires an image of the inspection target, which is placed on the inspection table, in a first direction along the inspection table, and a control unit that determines whether the articles in the inspection target overlap each other, based on inspection target information including appearance information of each of the articles forming the inspection target and the image of the inspection target in the first direction, and operates the vibration unit in a case in which it is determined that the articles overlap each other.

(2) An inspection method comprises a first imaging step of acquiring an image of an inspection target, which is a set of a plurality of articles placed on an inspection table, in a first direction along the inspection table, an overlap determination step of determining whether the articles in the inspection target overlap each other, based on inspection target information including appearance information of each of the articles forming the inspection target and the image of the inspection target in the first direction, and a first vibration step of vibrating the inspection table in a case in which it is determined in the overlap determination step that the articles overlap each other.

(3) A computer readable medium storing a program that causes a computer to perform each step of the inspection method according to (2) is provided.

According to the invention, it is possible to suitably and effectively arrange a plurality of articles on an inspection table.

DESCRIPTION OF THE PREFERRED EMBODIMENTS

Hereinafter, preferred embodiments of the invention will be described with reference to the drawings.

Figure 1:
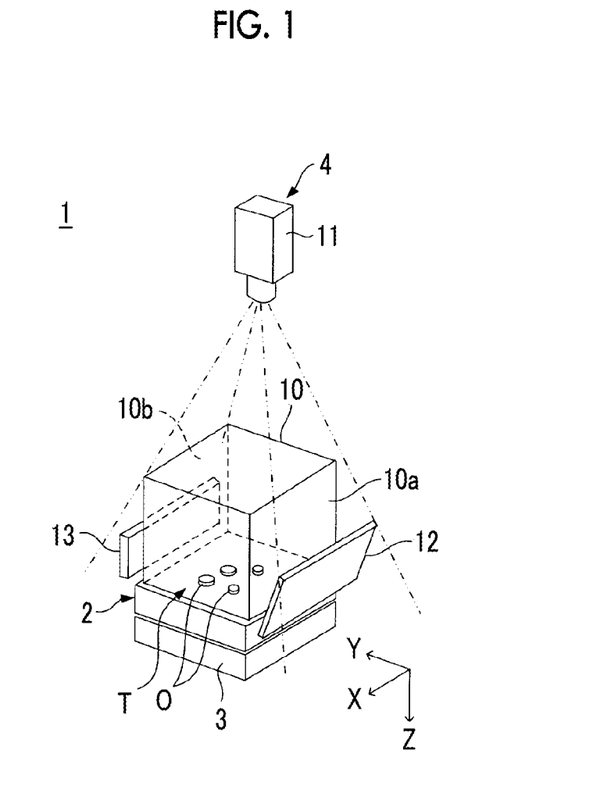
FIG. 1 is a diagram schematically illustrating the structure of an example of an inspection device in order to describe an embodiment of the invention.

FIG. 1 schematically illustrates the structure of an example of an inspection device in order to describe an embodiment of the invention.

An inspection device 1 illustrated in FIG. 1 inspects matching between a prescription and an inspection target T, which is a set of a plurality of solid drugs O corresponding to one packet, in a process of packaging solid drugs such as capsules or tablets. The inspection device 1 includes an inspection table 2, a vibration unit 3, and an imaging unit 4.

In the example illustrated in FIG. 1, the inspection table 2 includes a substantially rectangular tray 10 on which a set of a plurality of solid drugs O, which is the inspection target T, is placed. In the tray 10, at least a set of opposite side wall portions 10a and 10b is transparent. In the example illustrated in FIG. 1, the entire tray 10 is transparent. For example, the plurality of solid drugs O corresponding to one packet are collected by a pharmacist according to a prescription and are placed on the tray 10.

The vibration unit 3 vibrates the inspection table 2. For example, a known conductive vibration generator can be used as the vibration unit 3. When the inspection table 2 is vibrated by the vibration unit 3, the plurality of solid drugs O placed on the tray 10 are spread on the tray 10. In a case in which the solid drugs O overlap each other, the overlap is removed by the vibration.

The imaging unit 4 includes an imaging device 11, a mirror 12, and an illumination unit 13 and captures an image of the inspection target T placed on the tray 10 in a first direction (Y axis direction) in which the transparent side wall portions 10a and 10b of the tray 10 face each other and is along the bottom of the tray 10 on which the inspection target T is placed and a second direction (Z axis direction) in which the bottom of the tray 10 is seen straight. The term "looking straight at the bottom of the tray 10" includes a case in which a line of sight obliquely intersects an axis perpendicular to the bottom of the tray 10, that is, an axis perpendicular to the surface of the inspection table 2 on which the tray 10 is placed, in the same angle range as that in a case in which the line of sight is parallel to the axis.

The imaging device 11 is provided so as to face the bottom of the tray 10 straight. The field of view of the imaging device 11 includes the tray 10 and the mirror 12 is provided outside the tray 10 so as to be adjacent to the side wall portion 10a and is arranged in the field of view of the imaging device 11. The mirror 12 is arranged obliquely with respect to the first direction and the second direction so as to reflect an optical image of the inspection target T placed on the tray 10 in the first direction to the imaging device 11.

In the above-mentioned structure, an image which is acquired by one imaging operation using the imaging device 11 includes an image of the inspection target T in the second direction and an image of the inspection target T reflected in the mirror 12 in the first direction. The image of the inspection target T in the first direction and the image of the inspection target T in the second direction may be acquired by different imaging devices. However, the use of the mirror 12 makes it possible to acquire the image of the inspection target T in the first direction and the image of the inspection target T in the second direction using one imaging device 11. Therefore, the structure of the inspection device 1 is simplified.

The illumination unit 13 is provided outside the tray 10 such that it is adjacent to the side wall portion 10b and faces the mirror 12 in the first direction, with the tray 10 interposed therebetween, and illuminates the inspection target T placed on the tray 10 in the first direction from a side opposite to the mirror 12. Therefore, the capture of the image of the inspection target T by the imaging device 11 in the first direction is performed against the light and the image of the inspection target T in the first direction becomes a silhouette image. The image of the inspection target T in the first direction may be captured under environmental light. However, when imaging is performed against the light, the outline of the inspection target T is enhanced. It is preferable that the illumination unit 13 is a surface emission type in order to acquire a silhouette image.

Figure 2:
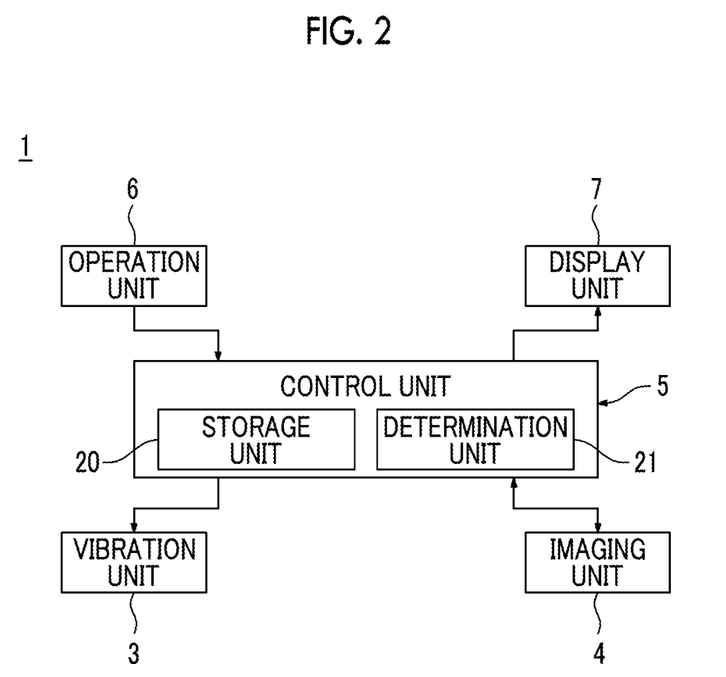
FIG. 2 is a diagram illustrating the functional block of the inspection device illustrated in FIG. 1.

FIG. 2 illustrates the functional block of the inspection device 1.

The inspection device 1 includes a control unit 5. The control unit 5 includes a central processing unit (CPU) as a main component, a storage unit 20, and a determination unit 21. In the example illustrated in FIG. 2, the inspection device 1 is provided with an operation unit 6 that receives a user operation and a display unit 7 that displays, for example, an inspection result.

The storage unit 20 stores programs executed by the control unit 5. The control unit 5 operates according to the program stored in the storage unit 20 and controls the overall operation of each unit of the inspection device 1 including the vibration unit 3 and the imaging unit 4. In this way, the inspection of the inspection target T by the inspection device 1 is performed.

In addition, the storage unit 20 stores inspection target information related to the inspection target T. In this example in which the consistency between a prescription and the inspection target T which is a set of the plurality of solid drugs O is inspected, the inspection target information includes a prescription, that is, the names of the solid drugs forming the inspection target T and the number of solid drugs, and appearance information of each drug.

For example, the names of the drugs and the number of drugs included in the inspection target information are input by the user through the operation unit 6 according to a prescription. For the appearance information of each drug included in the inspection target information, for example, a drug database that stores the appearance information of various types of drug is stored in the storage unit 20 in advance and the appearance information of the drugs matched with the drug names included in the inspection target information are collected from the drug database.

The appearance information of each drug includes information about the height of the drug in a stable posture where the center of gravity is the lowest and information about the outline of the drug in a case in which the drug in the stable posture is seen straight. In addition, in some cases, in order to identify drug, the surface of the drug is coated with various colors and, for example, numbers or symbols are provided in the surface of the drug by stamping or printing. The appearance information of each drug may include information, such as the color of the surface of the drug or numbers or symbols provided in the surface of the drug.

The determination unit 21 determines whether the solid drugs O in the inspection target T overlap each other on the basis of the inspection target information of the inspection target T and the image (silhouette image) of the inspection target T in the first direction which has been acquired by the imaging unit 4. In addition, the determination unit 21 determines whether the solid drug O in an unstable posture is present in the inspection target T, on the basis of the inspection target information of the inspection target T and the image of the inspection target T in the second direction which has been acquired by the imaging unit 4.

The control unit 5 appropriately operates the vibration unit 3 such that the solid drugs O included in the inspection target T are properly arranged on the tray 10 of the inspection table 2, on the basis of the result of determining whether the solid drugs O overlap each other and the result of determining whether there is a solid drug O in an unstable posture.

FIGS. 3A and 3B and FIGS. 4A and 4B illustrate examples of the solid drug O.

Figure 3A:
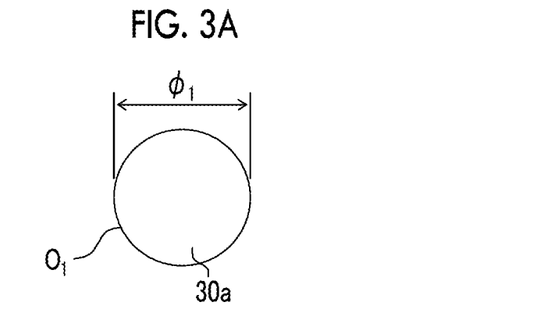
FIGS. 3A and 3B are diagrams illustrating an example of a solid drug.
Figure 3B:
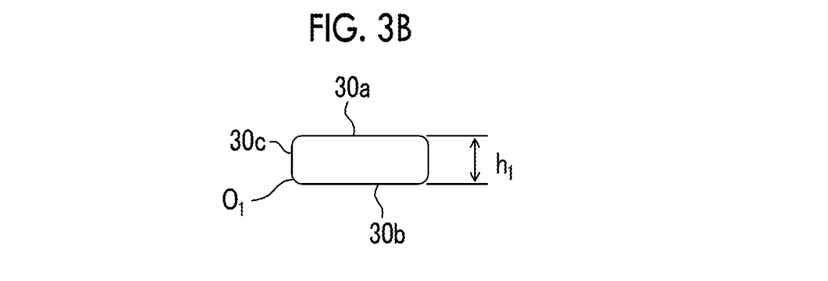

A solid drug $O_1$ illustrated in FIGS. 3A and 3B is a disk-shaped tablet, is in a stable posture where the center of gravity is the lowest in a state in which one of the flat front and rear surfaces 30a and 30b is grounded, and is in an unstable posture in a state in which a circumferential surface 30c is grounded. The appearance information of the solid drug $O_1$ includes the height $h_1$ of the drug when the drug is in the stable posture and includes outline information, such as the shape or size (diameter $\phi_1$) of the solid drug $O_1$, in a case in which one of the front and rear surfaces 30a and 30b is seen straight, that is, in a case in which the solid drug $O_1$ in the stable posture is seen straight.

Figure 4A:
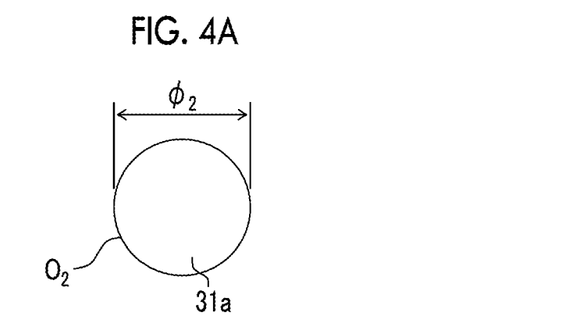
FIGS. 4A and 4B are diagrams illustrating another example of the solid drug.
Figure 4B:
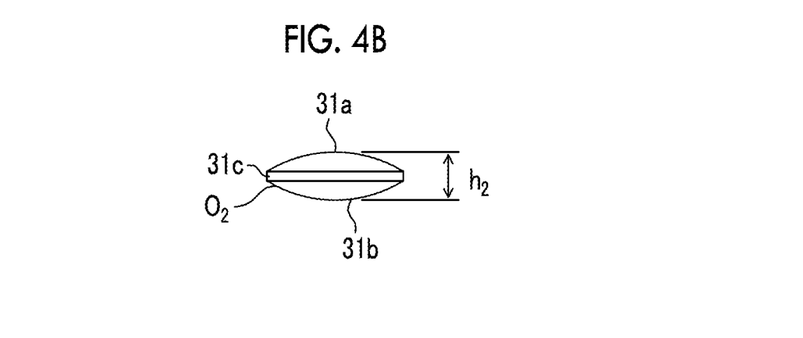

A solid drug $O_2$ illustrated in FIGS. 4A and 4B is a lens-shaped solid drug, is in a stable posture where the center of gravity is the lowest in a state in which one of circular front and rear surfaces 31a and 31b which are curved in a convex shape is grounded, and is in an unstable posture in a state in which a circumferential surface 31c is grounded. The appearance information of the solid drug $O_2$ includes the height $h_2$ of the drug when the drug is arranged in the stable posture and includes outline information, such as the shape or size (diameter $\phi_2$) of the solid drug $O_2$, in a case in which one of the front and rear surfaces 31a and 31b is seen straight, that is, in a case in which the solid drug $O_2$ in the stable posture is seen straight.

Figure 5:
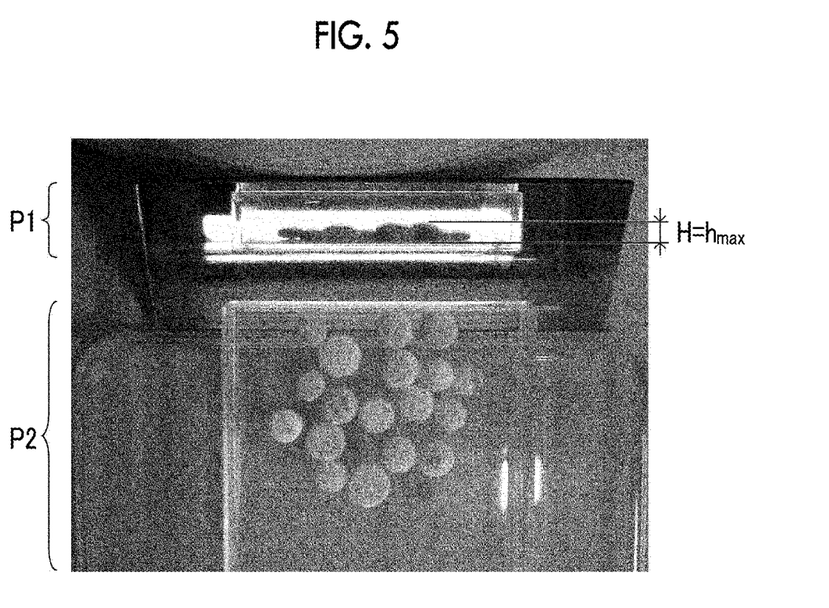
FIG. 5 is a diagram illustrating an example of an image of an inspection target which is acquired by an imaging unit of the inspection device illustrated in FIG. 1.
Figure 6:
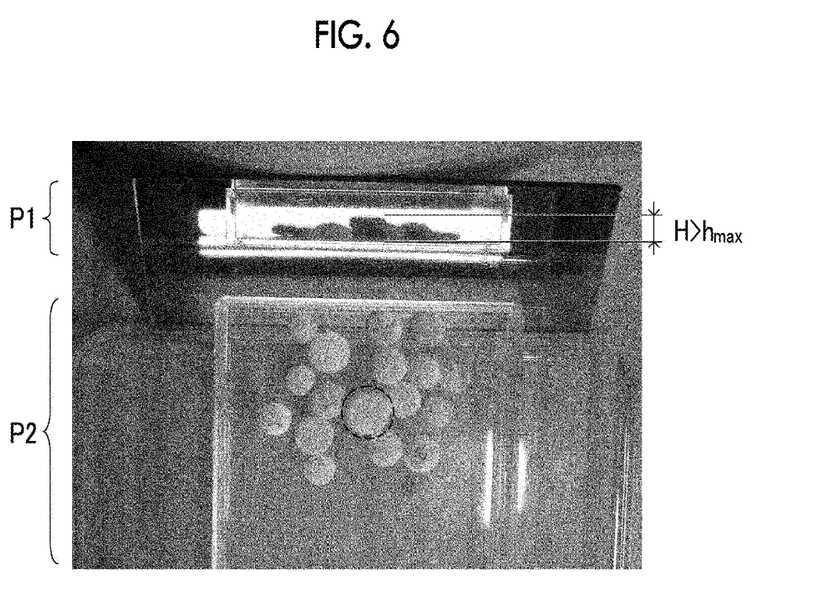
FIG. 6 is a diagram illustrating another example of the image of the inspection target which is acquired by the imaging unit of the inspection device illustrated in FIG. 1.
Figure 7:
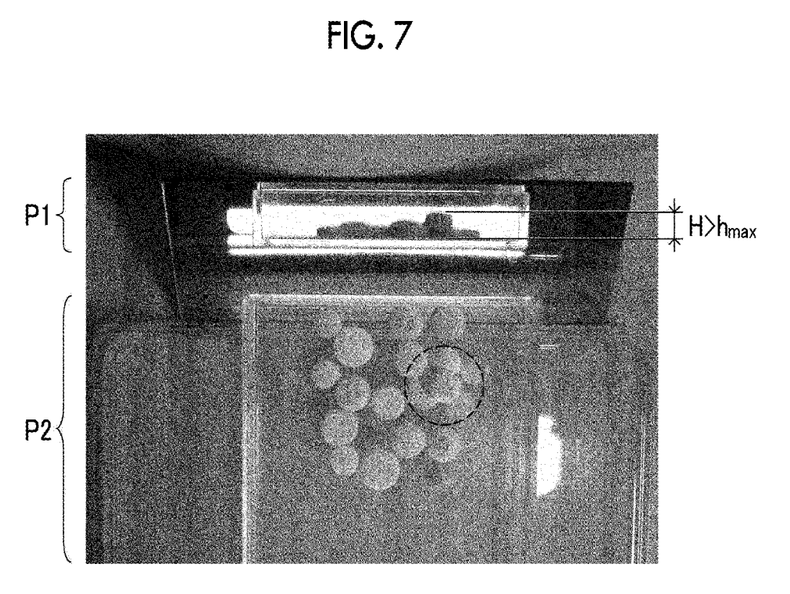
FIG. 7 is a diagram illustrating still another example of the image of the inspection target which is acquired by the imaging unit of the inspection device illustrated in FIG. 1.

FIGS. 5 to 7 illustrate examples of the image of the inspection target T acquired by the imaging unit 4. FIG. 5 illustrates a case in which the solid drugs O do not overlap each other in the inspection target T and FIGS. 6 and 7 illustrate a case in which the solid drugs O overlap each other in the inspection target T. In FIGS. 6 and 7, a group of the solid drugs O which overlap each other is represented by a dashed circle.

As described above, the image of the inspection target T acquired by the imaging unit 4 includes an image (silhouette image) P1 of the inspection target T in the first direction and an image P2 of inspection target T in the second direction.

The determination unit 21 of the control unit 5 determines whether the solid drugs O in the inspection target T overlap each other, on the basis of the inspection target information of the inspection target T and the image P1 of the inspection target T in the first direction which has been acquired by the imaging unit 4. Specifically, the determination unit 21 detects the maximum value H of the height position of the upper end of each solid drug O in the image P1 of the inspection target T in the first direction from the inspection table 2 (the bottom of the tray 10). Then, the determination unit 21 determines that the solid drugs O overlap each other in a case in which $H > h_{max}$ is satisfied (where $h_{max}$ is the maximum value of the height h of each drug included in the inspection target information of the inspection target T) and determines that the solid drugs O do not overlap each other in a case in which $H = h_{max}$ is established.

In addition, the determination unit 21 also performs gray determination that does not ensure the determination of no overlap in a case in which it is determined that the solid drugs O do not overlap each other and the height h of an arbitrary drug included in the inspection target information of the inspection target T satisfies $h \times 2 < h_{max}$, that is, the drugs having a relatively small height overlap each other and it is likely to be difficult to determine whether the drugs overlap each other according to the overlap determination process.

In addition, the determination unit 21 determines whether there is a solid drug O in the unstable posture in the inspection target T, on the basis of the inspection target information of the inspection target T and the image P2 of the inspection target T in the second direction which has been acquired by the imaging unit 4. Specifically, the determination unit 21 detects the outline of each solid drug O in the image P2 of the inspection target T in the second direction. Then, the determination unit 21 matches the detected outline of each solid drug with the outline information of each drug included in the inspection target information of the inspection target T, determines that there is a solid drug O in the unstable posture in a case in which one or more of the detected outlines are not matched with the outline information of each drug included in the inspection target information, and determines that there is no solid drug O in the unstable posture in a case in which all of the detected outlines are matched with the outline information of each drug included in the inspection target information.

Figure 8:
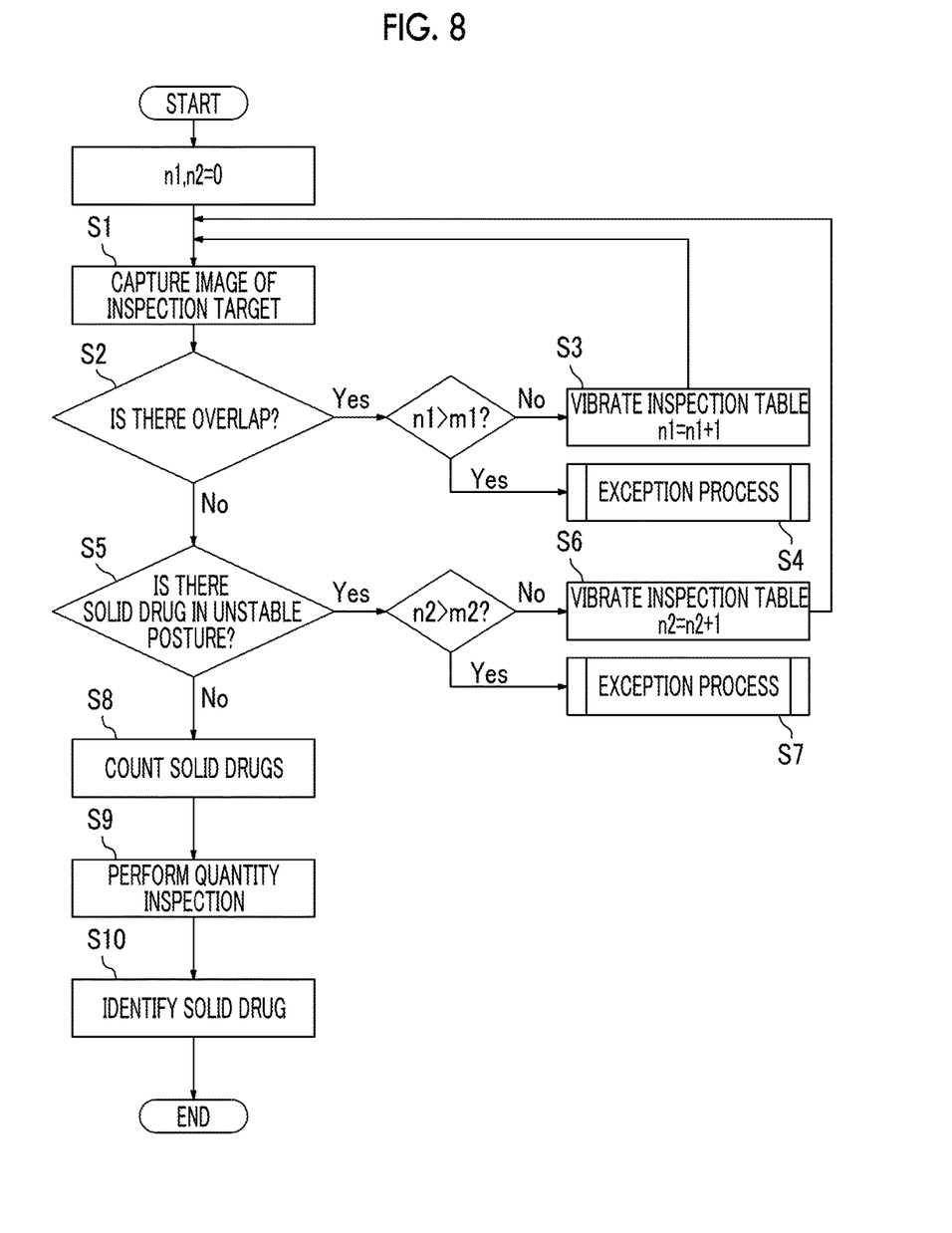
FIG. 8 is a diagram illustrating the operation flow of the inspection device illustrated in FIG. 1.

FIG. 8 illustrates the operation flow of the inspection device 1.

<Imaging Step>

First, the imaging unit 4 captures an image of the inspection target T and acquires the image of the inspection target T in the first direction, under the control of the control unit 5 (Step S1). In this example, the image of the inspection target T in the first direction and the image of the inspection target T in the second direction are acquired by one imaging operation using the imaging device 11 of the imaging unit 4 and the imaging step Si includes a first imaging step of acquiring the image of the inspection target T in the first direction and a second imaging step of acquiring the image of the inspection target T in the second direction.

<Overlap Determination Step>

The control unit 5 determines whether the solid drugs O in the inspection target T overlap each other, on the basis of the inspection target information of the inspection target T and the image of the inspection target T in the first direction acquired in the imaging step S1 (Step S2).

<First Vibration Step>

In a case in which it is determined that the solid drugs O overlap each other, the vibration unit 3 is operated to vibrate the inspection table 2 under the control of the control unit 5, in order to remove the overlap between the solid drugs O (Step S3).

Here, as in the example illustrated in FIG. 8, preferably, the control unit 5 is configured such that it counts the number of repetitions n1 (the number of times the inspection table 2 is vibrated) of the first vibration step S3 for one inspection target T and performs an exception process that gets out of the repetition of the first vibration step S3 and the overlap determination step S2 in a case in which the number of repetitions n1 is greater than a predetermined threshold value m1 (Step S4). For example, in a case in which a solid drug that is not written in the prescription is included in the inspection target T and the maximum value H of the height position of the upper end of each solid drug, which is in the image P1 of the inspection target T in the first direction, from the inspection table 2 is obtained due to the solid drugs, the exception process can prevent the vibration of the inspection table 2 from being unnecessarily repeated. For example, the exception process may be configured such that information indicating that the determination of whether drugs overlap each other is not ensured is displayed on the display unit 7 to call the user's attention to the fact and an inspection process for the inspection target T ends.

<Posture Determination Step>

Then, the control unit 5 determines whether there is a solid drug O in the unstable posture in the inspection target T, on the basis of the outline of each drug included in the inspection target information of the inspection target T and the image of the inspection target T in the second direction acquired in the imaging step S1 (Step S5).

<Second Vibration Step>

In a case in which there is a solid drug O in the unstable posture, the vibration unit 3 is operated to vibrate the inspection table 2 under the control of the control unit 5, in order to remove the unstable posture of the solid drug O (Step S6).

As in the example illustrated in FIG. 8, preferably, the control unit 5 is configured such that it counts the number of repetitions n2 of the second vibration step S6 for one inspection target T and performs an exception process that gets out of the repetition of the second vibration step S6 and the posture determination step S5 in a case in which the number of repetitions n2 is greater than a predetermined value m2 (Step S7). For example, in a case in which a solid drug that is not written in the prescription is included in the inspection target T, the exception process can prevent the vibration of the inspection table 2 from being unnecessarily repeated. For example, the exception process may be configured such that information indicating that the determination of whether there is a solid drug O in the unstable posture is displayed on the display unit 7 to call the user's attention to the fact and an inspection process for the inspection target T ends.

<Counting Step>

When it is determined that the solid drugs O do not overlap each other and there is no solid drug O in the unstable posture, the control unit 5 counts the solid drugs O included in the inspection target T on the basis of the image of the inspection target T in the second direction (Step S8).

In the counting of the solid drugs O, for example, the outline of each solid drug O in the image of the inspection target T in the second direction may be detected and the number of detected outlines may be counted. Since the solid drugs O do not overlap each other, the outlines of the solid drugs O detected from the image of the inspection target T in the second direction are independent and the number of detected outlines can be counted to count the number of solid drugs O.

The control unit 5 compares the count value of the solid drugs O with the number of drugs included in the inspection target information of the inspection target T to perform quantity inspection (Step S9). The inspection result is displayed on the display unit 7 under the control of the control unit 5. In a case in which gray determination that does not ensure the determination of no overlap is also performed, information indicating the fact is displayed on the display unit 7 to call the user's attention to the fact.

<Identifying Step>

In this example, the control unit 5 identifies each solid drug O included in the inspection target T on the basis of the inspection target information of the inspection target T and the image of the inspection target T in the second direction (Step S10).

In the identification of the solid drug O, for example, the outline of each solid drug O in the image of the inspection target T in the second direction may be detected and the matching between each of the detected outlines and the outline information of each drug included in the inspection target information of the inspection target T may be performed to determine the drug that is matched with the outline information.

In a case in which the appearance information of each drug included in the inspection target information includes information about the color of the surface of the drug or information about numbers or symbols provided on the surface, these information items can be used to identify the solid drug O. In particular, the numbers or symbols on the surface of the drug are typically provided on the surface of the drug which faces upward when the drug is in the stable posture. Each solid drug O included in the inspection target T is arranged in the stable posture on the inspection table 2 through the posture determination step S5 and the second vibration step S6. Therefore, it is possible to check the numbers or symbols on the surface of each solid drug O from the front side, using the imaging device 11 of the imaging unit 4 which is provided so as to face the inspection table 2 straight. As a result, it is possible to accurately identify the numbers or symbols on the surface of each solid drug O.

When the solid drug O is identified, it is possible to check the number of solid drugs O of each type included in the inspection target T. For example, when the number of solid drugs O of a certain type is greater or smaller than a predetermined value, it is possible to rapidly correct the number of solid drugs O of this type.

In this example, the solid drug O is identified. However, when only quantity inspection is performed, the posture determination step S5 and the second vibration step S6 may be omitted.

In the above-mentioned operation flow of the inspection device 1, it is determined whether the solid drugs O in the inspection target T overlap each other on the basis of the inspection target information of the inspection target T and the image of the inspection target T in the first direction and the inspection table 2 is vibrated in a case in which it is determined that the solid drugs O overlap each other. Therefore, it is possible to prevent the unnecessary vibration of the inspection table 2, to appropriately and effectively arrange a plurality of solid drugs O included in the inspection target T on the inspection table 2, and to reduce the time required to inspect the inspection target T.

The embodiment of the invention in which the inspection target T is a set of a plurality of solid drugs O corresponding to one packet has been described above. However, the inspection target is not limited to a set of a plurality of solid drugs. For example, in some cases, each set of relatively small mechanical components, such as screws or nuts, is packaged. A set of mechanical components corresponding to one packet may be used as the inspection target.

As described above, the specification discloses the following matters.

(1) An inspection device comprises an inspection table on which an inspection target which is a set of a plurality of articles is placed, a vibration unit that vibrates the inspection table, an imaging unit that acquires an image of the inspection target, which is placed on the inspection table, in a first direction along the inspection table, and a control unit that determines whether the articles in the inspection target overlap each other, on the basis of inspection target information including appearance information of each of the articles forming the inspection target and the image of the inspection target in the first direction, and operates the vibration unit in a case in which it is determined that the articles overlap each other.

(2) In the inspection device according to (1), the appearance information includes height information of each of the articles when the article is in a stable posture where the center of gravity is the lowest. When a maximum value of a height position of an upper end of each of the articles, which is in the image of the inspection target in the first direction, from the inspection table is H and a maximum value of the height of each of the articles included in the inspection target information is $h_{max}$, the control unit determines that the articles overlap each other in a case in which $H > h_{max}$ is satisfied.

(3) The inspection device according to (1) or (2) further comprises an illumination unit that illuminates the inspection target in the first direction from a side opposite to the imaging unit. The imaging unit acquires a silhouette image of the inspection target as the image of the inspection target in the first direction.

(4) In the inspection device according to any one of (1) to (3), the imaging unit further acquires an image of the inspection target, which is placed on the inspection table, in a second direction in which the inspection table is seen straight. In a case in which it is determined that the articles do not overlap each other, the control unit counts the articles included in the inspection target on the basis of the image of the inspection target in the second direction.

(5) In the inspection device according to (4), the inspection target information includes information about the number of articles forming the inspection target. The control unit compares the number of articles included in the inspection target information with the number of articles which is counted on the basis of the image of the inspection target in the second direction to perform quantity inspection.

(6) In the inspection device according to (4) or (5), the appearance information includes outline information of each of the articles in a case in which each of the articles in the stable posture where the center of gravity is the lowest is seen straight. The control unit determines whether there is an article in an unstable posture in the inspection target, on the basis of the outline of each of the articles included in the inspection target information and the image of the inspection target in the second direction, and operates the vibration unit in a case in which it is determined that there is an article in the unstable posture.

(7) In the inspection device according to (6), in a case in which it is determined that the articles do not overlap each other and there are no articles in the unstable posture, the control unit identifies each of the articles included in the inspection target on the basis of the appearance information of each of the articles included in the inspection target information and the image of the inspection target in the second direction.

(8) In the inspection device according to any one of (4) to (7), the imaging unit includes an imaging device that is provided so as to face the inspection table straight and a mirror that is provided in a field of view of the imaging device and reflects an optical image of the inspection target in the first direction to the imaging device.

(9) In the inspection device according to any one of (1) to (8), the article is a solid drug and the inspection target is a set of a plurality of solid drugs corresponding to one packet.

(10) An inspection method comprises a first imaging step of acquiring an image of an inspection target, which is a set of a plurality of articles placed on an inspection table, in a first direction along the inspection table, an overlap determination step of determining whether the articles in the inspection target overlap each other, on the basis of inspection target information including appearance information of each of the articles forming the inspection target and the image of the inspection target in the first direction, and a first vibration step of vibrating the inspection table in a case in which it is determined in the overlap determination step that the articles overlap each other.

(11) In the inspection method according to (10), the appearance information includes height information of each of the articles when the article is in a stable posture where the center of gravity is the lowest. When a maximum value of a height position of an upper end of each of the articles, which is in the image of the inspection target in the first direction, from the inspection table is H and a maximum value of the height of each of the articles included in the inspection target information is $h_{max}$, it is determined in the overlap determination step that the articles overlap each other in a case in which $H > h_{max}$ is satisfied.

(12) The inspection method according to (10) or (11) further comprises a second imaging step of acquiring an image of the inspection target, which is placed on the inspection table, in a second direction in which the inspection table is seen straight and a counting step of counting the articles included in the inspection target on the basis of the image of the inspection target in the second direction in a case in which it is determined in the overlap determination step that the articles do not overlap each other.

(13) In the inspection method according to (12), the appearance information includes outline information of each of the articles in a case in which each of the articles in the stable posture where the center of gravity is the lowest is seen straight. The inspection method further comprises a posture determination step of determining whether there is an article in an unstable posture in the inspection target, on the basis of the outline of each of the articles included in the inspection target information and the image of the inspection target in the second direction and a second vibration step of vibrating the inspection table in a case in which it is determined in the posture determination step that there is an article in the unstable posture.

(14) In the inspection method according to (13), in a case in which it is determined in the overlap determination step that the articles do not overlap each other and it is determined in the posture determination step that there are no articles in the unstable posture, each of the articles included in the inspection target is identified on the basis of the appearance information of each of the articles included in the inspection target information and the image of the inspection target in the second direction.

(15) In the inspection method according to any one of (10) to (14), the number of repetitions of the first vibration step for one inspection target is counted. The inspection method further comprises an exception process step that gets out of the repetition of the first vibration step and the overlap determination step in a case in which it is determined in the overlap determination step that the articles overlap each other and in a case in which the number of repetitions is greater than a predetermined threshold value.

(16) In the inspection method according to (13) or (14), the number of repetitions of the second vibration step for the one inspection target is counted. The inspection method further comprises an exception process step that gets out of the repetition of the second vibration step and the posture determination step in a case in which it is determined in the posture determination step that there is an articles in the unstable posture and in a case in which the number of repetitions is greater than a predetermined threshold value.

(17) A program causes a computer to perform each step of the inspection method according to any one of (10) to (16).

INDUSTRIAL APPLICABILITY

The invention can be used in a case in which a set of a plurality of articles, which are a plurality of solid drugs or relatively small mechanical components, such as screws or nuts, is packaged into a packet and it is determined whether the articles are exactly inserted into each packet.

The embodiment of the invention has been described in detail above. However, the embodiment is illustrative and various modifications and changes of the invention can be made without departing from the scope and spirit of the invention. This application is based on Japanese Patent Application No. 2014-038727 filed Feb. 28, 2014, the entire content of which is hereby incorporated by reference.

EXPLANATION OF REFERENCES

1: inspection device
2: inspection table
3: vibration unit
4: imaging unit
5: control unit
6: operation unit
7: display unit
10: tray
10a: side wall portion
10b: side wall portion
11: imaging device
12: mirror
13: illumination unit
20: storage unit
21: determination unit
O: solid drug (article)
P1: image in first direction
P2: image in second direction
T: inspection target

What is claimed is:

1. An inspection device comprising:
an inspection table on which an inspection target which is a set of a plurality of articles is placed; and
at least one hardware processor configured to implement:
a vibration unit that vibrates the inspection table;
an imaging unit that acquires an image of the inspection target, which is placed on the inspection table, in a first direction along the inspection table; and
a control unit that determines whether the articles in the inspection target overlap each other, based on inspection target information comprising appearance information of each of the articles forming the inspection target and the image of the inspection target in the first direction, and operates the vibration unit in a case in which it is determined that the articles overlap each other,
wherein the appearance information comprises height information of each of the articles when the article is in a stable posture where the center of gravity is the lowest, and
when a maximum value of a height position of an upper end of each of the articles, which is in the image of the inspection target in the first direction, from the inspection table is H and a maximum value of the height of each of the articles included in the inspection target information is hmax, the control unit determines that the articles overlap each other in a case in which H >hmax is satisfied.

2. The inspection device according to claim 1, wherein the at least one hardware processor is further configured to implement:
an illumination unit that illuminates the inspection target in the first direction from a side opposite to the imaging unit,
wherein the imaging unit acquires a silhouette image of the inspection target as the image of the inspection target in the first direction.

3. The inspection device according to claim 1,
wherein the imaging unit further acquires an image of the inspection target, which is placed on the inspection table, in a second direction in which the inspection table is seen straight, and
in a case in which it is determined that the articles do not overlap each other, the control unit counts the articles included in the inspection target based on the image of the inspection target in the second direction.

4. The inspection device according to claim 3,
wherein the inspection target information comprises information about number of articles forming the inspection target, and
the control unit compares the number of articles included in the inspection target information with the number of articles which is counted based on the image of the inspection target in the second direction to perform quantity inspection.

5. The inspection device according to claim 3,
wherein the appearance information comprises outline information of each of the articles in a case in which each of the articles in a stable posture where the center of gravity is the lowest is seen straight, and
the control unit determines whether there is an article in an unstable posture in the inspection target, based on the outline of each of the articles included in the inspection target information and the image of the inspection target in the second direction, and operates the vibration unit in a case in which it is determined that there is an article in the unstable posture.

6. The inspection device according to claim 5,
wherein, in a case in which it is determined that the articles do not overlap each other and there are no articles in the unstable posture, the control unit identifies each of the articles included in the inspection target based on the appearance information of each of the articles included in the inspection target information and the image of the inspection target in the second direction.

7. The inspection device according to claim 3,
wherein the imaging unit comprises:
an imaging device that is provided so as to face the inspection table straight; and
a mirror that is provided in a field of view of the imaging device and reflects an optical image of the inspection target in the first direction to the imaging device.

8. The inspection device according to claim 1,
wherein the article is a solid drug, and
the inspection target is a set of a plurality of solid drugs corresponding to one packet.

9. An inspection method comprising:
implementing by at least one hardware processor:
a first imaging step of acquiring an image of an inspection target, which is a set of a plurality of articles placed on an inspection table, in a first direction along the inspection table;
an overlap determination step of determining whether the articles in the inspection target overlap each other, based on inspection target information comprising appearance information of each of the articles forming the inspection target and the image of the inspection target in the first direction; and
a first vibration step of vibrating the inspection table in a case in which it is determined in the overlap determination step that the articles overlap each other,
wherein the appearance information comprises height information of each of the articles when the article is in a stable posture where the center of gravity is the lowest, and
when a maximum value of a height position of an upper end of each of the articles, which is in the image of the inspection target in the first direction, from the inspection table is H and a maximum value of the height of each of the articles included in the inspection target information is hmax, it is determined in the overlap determination step that the articles overlap each other in a case in which H >hmax is satisfied.

10. The inspection method according to claim 9, further comprising:
implementing by the at least one hardware processor:
a second imaging step of acquiring an image of the inspection target, which is placed on the inspection table, in a second direction in which the inspection table is seen straight; and
a counting step of counting the articles included in the inspection target based on the image of the inspection target in the second direction in a case in which it is determined in the overlap determination step that the articles do not overlap each other.

11. The inspection method according to claim 10,
wherein the appearance information comprises outline information of each of the articles in a case in which each of the articles in the stable posture where the center of gravity is the lowest is seen straight, and
the inspection method further comprises:
implementing by the at least one hardware processor:
a posture determination step of determining whether there is an article in an unstable posture in the inspection target, based on the outline of each of the articles included in the inspection target information and the image of the inspection target in the second direction; and
a second vibration step of vibrating the inspection table in a case in which it is determined in the posture determination step that there is an article in the unstable posture.

12. The inspection method according to claim 11,
wherein, in a case in which it is determined in the overlap determination step that the articles do not overlap each other and it is determined in the posture determination step that there are no articles in the unstable posture, each of the articles included in the inspection target is identified based on the appearance information of each of the articles included in the inspection target information and the image of the inspection target in the second direction.

13. The inspection method according to claim 11,
wherein number of repetitions of the second vibration step for the one inspection target is counted, and
the inspection method further comprises, implementing by the at least one hardware processor, an exception process step that gets out of the repetition of the second vibration step and the posture determination step in a case in which it is determined in the posture determination step that there is an articles in the unstable posture and in a case in which the number of repetitions is greater than a predetermined threshold value.

14. The inspection method according to claim 9,
wherein number of repetitions of the first vibration step for one inspection target is counted, and
the inspection method further comprises, implementing by the at least one hardware processor, an exception process step that gets out of the repetition of the first vibration step and the overlap determination step in a case in which it is determined in the overlap determination step that the articles overlap each other and in a case in which the number of repetitions is greater than a predetermined threshold value.

15. A computer readable medium storing a program that causes a computer to perform each step of the inspection method according to claim 9.

* * * * *